United States Patent [19]
Camborde et al.

[11] Patent Number: 6,015,797
[45] Date of Patent: Jan. 18, 2000

[54] ADENOSINERGIC AGONIST CONTAINING PHARMACEUTICAL COMPOSITION WITH ANALGESIC ACTIVITY

[75] Inventors: Francoise Camborde, Rueil Malmaison; Alix Cloarec, Triel Sur Siene, both of France; Timur Gungor, Brandon Farms, N.J.; Jean-Marie Teulon, La Celle Saint Cloud, France

[73] Assignee: Laboratoires UPSA, Agen, France

[21] Appl. No.: 09/206,536

[22] Filed: Dec. 7, 1998

[30] Foreign Application Priority Data

Dec. 11, 1997 [FR] France ................... 97/15685

[51] Int. Cl.$^7$ ............ A61K 31/70; A61K 31/55; A61K 31/44
[52] U.S. Cl. ............ 514/46; 514/221; 514/289; 536/27.62; 540/550; 546/44
[58] Field of Search ............... 514/46, 221, 282, 514/289; 536/27.62; 540/550; 546/44

[56] References Cited

U.S. PATENT DOCUMENTS

| | | |
|---|---|---|
| 5,229,505 | 7/1993 | Bru-Magniez, I et al. ......... 536/27.62 |
| 5,480,983 | 1/1996 | Bru-Magniez, II et al. ........ 536/27.62 |
| 5,677,290 | 10/1997 | Fukunaga .................... 514/46 |

FOREIGN PATENT DOCUMENTS

| | | |
|---|---|---|
| 0623138 | 11/1994 | European Pat. Off. . |
| 0797992 | 10/1997 | European Pat. Off. . |

OTHER PUBLICATIONS

A.G. Goodman et al. (eds.), *The Pharmaceutical Basis of Therapeutics, 8th Edition,* Pergamon Press, New York, NY, 1990, only title & text pp. 256–258 and 303–304 supplied.

Schillinger et al., "Metabolic Effects of $N^6$–Substituted Adenosines in Rats," *Biochemical Pharmacology,* 23, 2283–2289 (Aug. 15, 1974).

Kikugawa et al., "Platelet Aggregation Inhibitors. 4. $N^{6-Substituted\ Adenosines}$," *J. Medicinal Chemistry,* 16(4), 358–364 (Apr. 1973).

Frink et al., "Influence of Tramadol on Neurotransmitter Systems of the Rat Brain," *Arzn. Forschung/Drug Design,* 46(11), 1029–1036 (1996).

Berkow et al., (eds.), *The Merck Manual of Diagnosis and Therapy, 16th Ed..* Merck Research Labs., Div. of Merck & Co., Inc. Rahway, NJ, 1992, see Ch. 119, pp. 1409–1416.

*Primary Examiner*—L. Eric Crane
*Attorney, Agent, or Firm*—Barry J. Marenberg

[57] ABSTRACT

The object of the present invention is a pharmaceutical composition, which comprises, as active principle, a combination of an adenosinergic agonist and a compound selected from the opiates, benzodiazepines and NMDA antagonists.

6 Claims, 5 Drawing Sheets

Antinociceptive effect of intraperitoneal UP 202-39 and morphine combination in the hot plate test (56°C) in mice

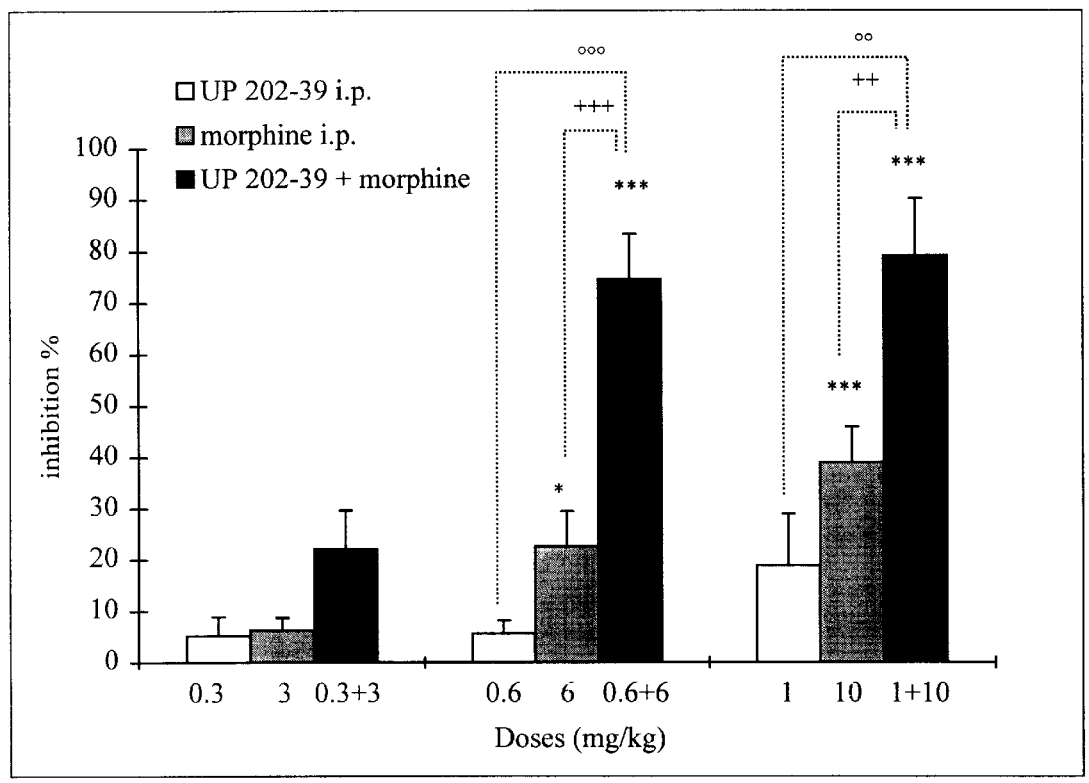

Dunnett's test: * and *** indicate a significant difference in comparison to the control group for P<0.05 and P<0.001, respectively.
Student's t test:
++ and +++ indicate a significant difference between the combination and the morphine group for P<0.01 and P<0.001, respectively.
°° and °°° indicate a significant difference between the combination and the UP 202-39 group for p<0.01 and P<0.001, respectively.
n = 10 per group

Figure 1

Antinociceptive effect of UP 202-56 and morphine combination in the hot plate test (56°C) in mice

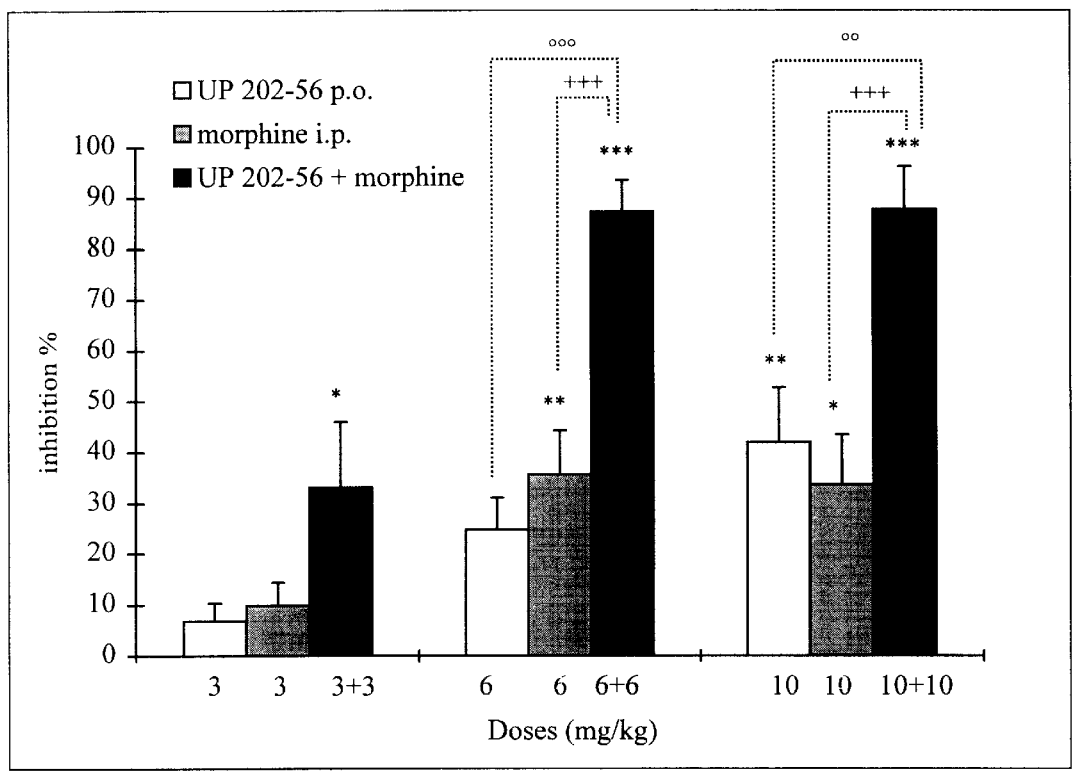

Dunnett's test: *,  and * indicate a significant difference in comparison to the control group for $P<0.05$, $P<0.01$ and $P<0.001$, respectively.
Student's t test:
+++ indicates a significant difference between the combination and the morphine group for $P<0.001$.
°° and °°° indicate a significant difference between the combination and the UP 202-56 group for $P<0.01$ and $P<0.001$, respectively.
n = 10 per group

Figure 2

Effect of diazepam (10 mg/kg i.p) on UP 202-56-induced antinociception in the hot plate test (56°C) in mice Dunnett's test:  and * indicate a significant difference in comparison to the control group for $P<0.01$ and $P<0.001$, respectively.
n = 10 per group

ADENOSINERGIC AGONIST CONTAINING PHARMACEUTICAL COMPOSITION WITH ANALGESIC ACTIVITY

The object of the present invention is a novel pharmaceutical combination which especially finds application in the treatment of various types of pain which can be of inflammatory origin or neuropathic origin. More specifically, the invention relates to a pharmaceutical composition which comprises, as active principle, a combination of an adenosinergic agonist and a compound selected from the opiates, benzodiazepines and NMDA antagonists.

It is known that adenosine is an endogenous molecule which participates in the regulation of many functions, in the central nervous system and peripherally, via the activation of specific receptors (Daly, I. W. in: T. W. Stone (Ed.) Purines Pharmacological and Physiological Roles, Macmillan, London. 1985: pp. 5–15).

The inhibitory role of adenosine in the modulation of the transmission of the pain message is now well-established (Sawynok, J., M. I. Sweeney. Neurosci. 1989;(32):557–569).

Many pharmacological studies have demonstrated the analgesic activity of adenosine and its analogues (M., Holmgren, J. Hedner, T. Mellstrand, G. Nordberg, Th. Hedner. Naunym-Schmicdeberg's Arch. Pharmacol. 1986; (334):290–293 ; and K., Herrick-Davis, S. Chippari, D. Luttinger, S. J. Ward. Eur. J. Pharrnacol. 1989; 162 :365–369.

However, for the majority, these compounds induce, at active doses, nonnegligible side effects, in particular cardiovascular side effects, which have hitherto limited their use.

Research has enabled developing adenosinergic agonist compounds which are active in animal acute or chronic pain models and which are devoid of major side effects at active doses.

Such compounds have, for example, been described in the document EP 623138 by the Applicant company.

Furthermore, it is known that opiate or morphinic compounds are powerful centrally acting analgesics which are indicated in the treatment of moderate to severe pain. These compounds can however induce tolerance and dependence in certain circumstances.

It is further known that benzodiazepines possess anxiolitic, muscle relaxing, anti-convulsivant and hypnotic properties.

Finally, it is known that the activation of N-methyl-D-aspartate (NMDA) receptors by neuro-excitatory amino acids (aspartate, glutamate) is implicated in certain pain processes.

NMDA antagonists thus possess an analgesic activity which is demonstrated in many tests, including chronic pain tests.

It has been discovered, and this constitutes the basis of the present invention, that the combination of an adenosinergic agonist and a compound selected from the opiates, benzodiazepines and NMDA antagonists, possesses a significant analgesic effect at doses at which each one of the products constituting this combination is inactive or not very active.

The beneficial effect of the combination in accordance with the present invention has been demonstrated both in inflammatory pain models and in noninflammatory acute pain models.

The results obtained have shown that this combination possesses an analgesic activity very much greater than that of each one of its constituent products used alone at the same dose.

The potentiation effect thus demonstrated renders the use of low doses of each one of the constituent products of the combination possible, thereby limiting their possible side effects, and increasing their therapeutic index. Moreover, this combination enables treating pain of very varied origin in a larger number of patients.

Advantageously, the pharmaceutical combination in accordance with the present invention will be in a form suitable for an administration:

via the oral route, such as simple or coated tablets, capsules or granules, for example;

via the rectal route, such as suppositories for example via the parenteral route, such as injectable preparations for example via the ocular route, such as eye lotions or ophthalmic solutions for example;

via the transdermal route, such as a patch, an ointment or a gel for example;

via the nasal route, such as aerosols and sprays for example; or via the auricular route, such as drops for example.

Such a composition can be prepared, according to the methods known per se, by incorporating the active principle, consisting of the above-mentioned combination, with excipients usually used such as talc, gum arabic, lactose, starch, magnesium stearate, polyvidone, cellulose derivatives, cocoa butter, semi-synthetic glycerides, aqueous or non-aqueous vehicles, fats of animal or vegetable origin, glycols, wetting agents, dispersing agents or emulsifiers, silicone gels, certain polymers or co-polymers, preservatives, flavours and coloring agents.

In general, any adenosinergic agonist compound can be used within the context of the present invention. Preferably, adenosine derivatives will be used such as those described in the document EP 623138 which corresponds to U.S. Pat. Nos. 5,229,505 and 5,480,983 of the Applicant company which are incorporated herein by reference.

A particularly preferred compound is N-cyclopropyl-1-deoxy-1-[6-[[2-[1[(2,5-dimethylphenyl)methyl]-5-methyl-1H-indol-3-yl]ethyl]amino]-9H-purin-9-yl]β-D-ribofuranuronamide, known under the code name UP 202-56.

Another particularly preferred compound is N-cyclopropyl-1-deoxy-1-[6[[2-[1-[2-(1-piperidinyl)ethyl]-1H-indol-3-yl]ethyl]amino]-9H-purin-9-yl]β-D-ribofuranuronamide, known under the code name UP 202-39.

Opiates which can be used within the context of the present invention can be of different nature: powerful opiates, of which the strongest is morphine, which can treat severe pain, such as using morphine itself or oxycodone, hydromorphone or hydrocodone; or weak opiates, which can treat pain of moderate intensity, such as codeine or dextropropoxyphen.

Derivatives having a powerful central analgesic effect will more particularly be preferred, morphine itself in particular.

The benzodiazepines which can be used within the context of the present invention can be of various nature such as prazepam, bromazepam, chlordiazepoxide, lorazepam or clobazam.

Diazepam will more particularly be preferred.

Dextromethorphan, ketamine, dizocilpine or phencyclidine will be cited in particular amongst the NMDA antagonists which can be used within the context of the present invention.

Dextromethorphan will more particularly be preferred.

Advantageously, the pharmaceutical compositions according to the invention will be presented in the form of a unit dose.

In the pharmaceutical combination in accordance with the present invention, the weight ratio of the adenosinergic agonist compound to the compound selected from the opiates, benzodiazepines and NMDA antagonists, will be that which has the best synergy between the two compounds combined. For the majority of the examples, it will be between 0.01 and 10, and will preferably be between 0.1 and 1.

The daily dose which can be employed of the various compounds which constitute the pharmaceutical combination in accordance with the invention will of course depend upon the state of the patient to be treated.

A suitable daily dose of adenosinergic agonist compound will generally be between about 10 mg and about 500 mg.

The pharmaceutical compositions in accordance with the present invention are suitable for the treatment of pain of inflammatory origin or of neuropathic origin.

Their use can, for example, be cited in the treatment of arthritis, especially rheumatoid arthritis, spondylitis, gouty arthritis, ostcoarthritis, juvenile arthritis, autoimmune diseases and lupus erythematosus.

These compositions can also be used within the context of the treatment of bronchial asthma, dysmenorrhea, tendinitis, bursitis, dermatological inflammations such as psoriasis, eczema, burns and dermatitis.

These compositions can also be used within the context of the treatment of gastrointestinal inflammations, Crohn's disease, gastritis and ulcerative colitis; in the prevention of cancer, especially adenocarcinoma of the colon; in the prevention of neurodegenerative diseases, particularly Alzheimer's disease; in the prevention of stroke and epilepsy, and in the prevention of premature labour.

These compositions can be used within the context of the treatment of pain symptoms, and especially in the treatment of myalgia or articular pain, dental pain, migraine, rheumatic complaints, pain of cancerous origin, and also as complementary treatments for infectious and febrile states.

Finally, these compositions can be used within the context of the treatment of neuropathic pain and in particular neuralgia, herpes, deafferentation pain, and diabetic neuropathies.

The invention even covers a method of therapeutic treatment of mammals, characterised in that it consists in administering to said mammal a therapeutically effective amount of a combination of an adenosinergic agonist compound and a compound selected from the opiates, benzodiazepines and NMDA antagonists as defined above.

This method especially enables treating pain of inflammatory or neuropathic origin.

DESCRIPTION OF THE DRAWINGS

FIG. 1 graphically illustrates the antinociceptive effect of intraperitoneal UP 202-39 and morphine combination in the hot plate test (56° C.) in mice;

FIG. 2 graphically illustrates the antinociceptive effect of UP 202-56 and morphine combination in the hot plate test (56° C.) in mice;

DEMONSTRATION OF THE ANALGESIC

PROPERTIES OF THE PHARMACEUTICAL

COMBINATION IN ACCORDANCE WITH THE INVENTION

In order to demonstrate the specific analgesic properties of the pharmaceutical combination in accordance with the present invention, several pharmacological tests have been performed whose experimental protocols and results obtained are given below.

In these tests, the compounds used as examples of an adenosinergic agonist are the compounds known:

under the codename UP-202-39 having the following formula:

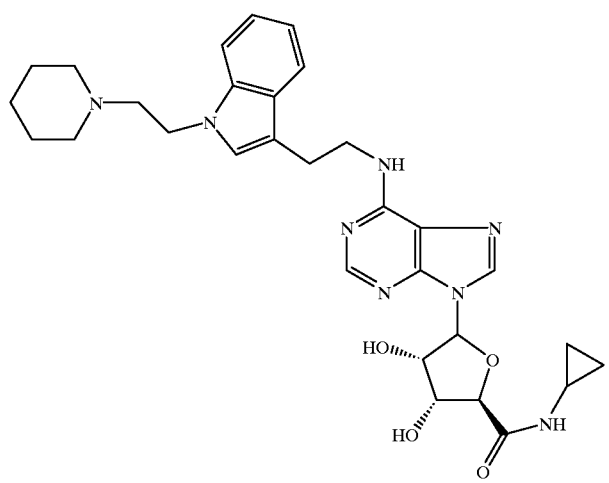

under the codename UP-202-56 having the following general formula:

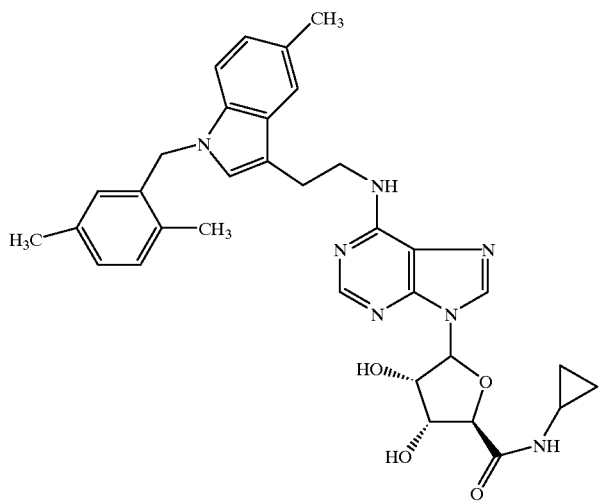

Test used: Heated Plate Test

This test is carried out by following the experimental protocol described by N. B. Eddy, C.F. Toucheberry and J. E. Uebemian, Synthetic Analgesics.

1-Methadone Isomers and Derivatives, J. Pharmacol. Exp. Ther. 1950 ; (98): 121–137.

The mouse disposed on a plate heated to 56° C.±0.05 shows its pain by licking its front paws, or more rarely by a jump.

The reaction time is then noted down, the maximum time being 30 seconds.

The compounds or combinations studied are administered via the oral route or via the intraperitoneal route one hour or thirty minutes respectively before the test.

Figure 3:
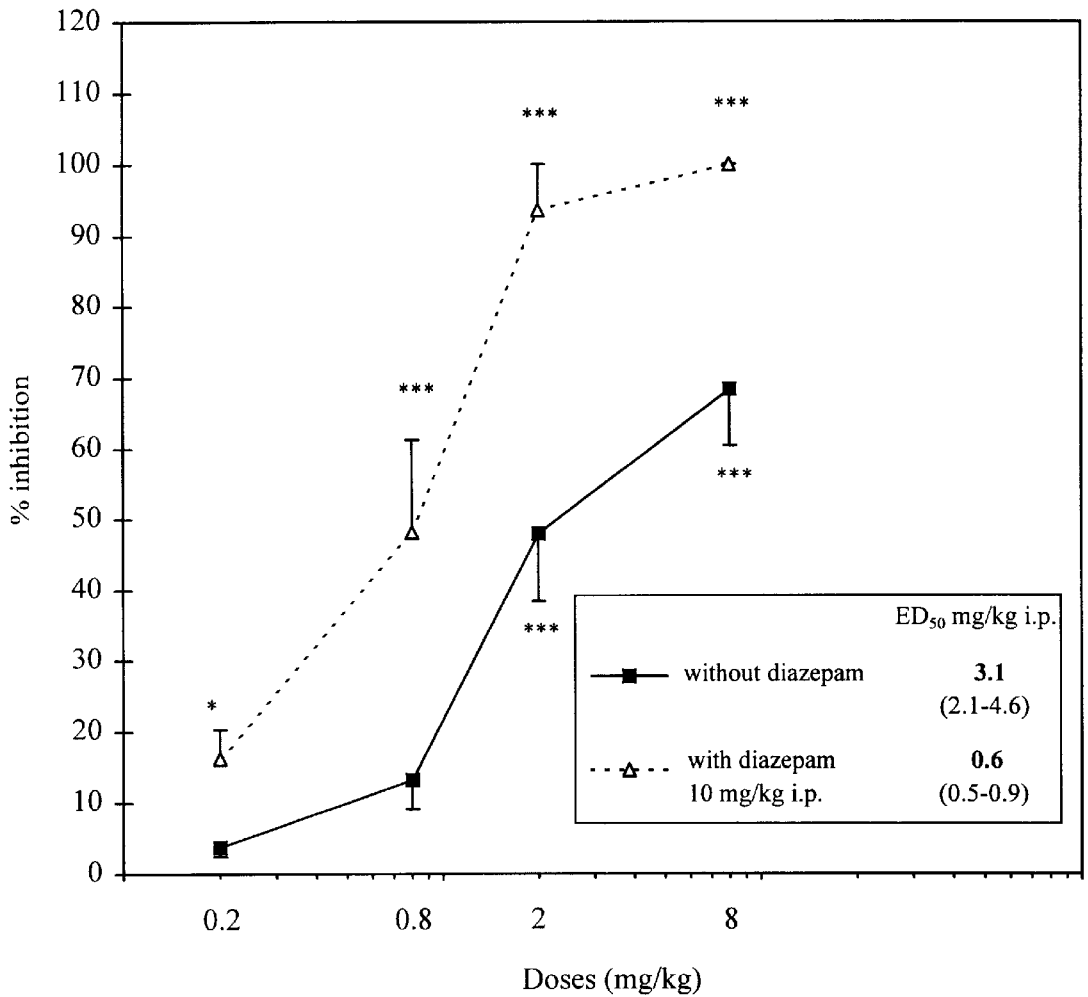
FIG. 3 graphically illustrates the effect of diazepam (10 mg/kg i.p.) on UP 202-39-induces antinociception in the hot plate test (56° C.) in mice.
Figure 4:
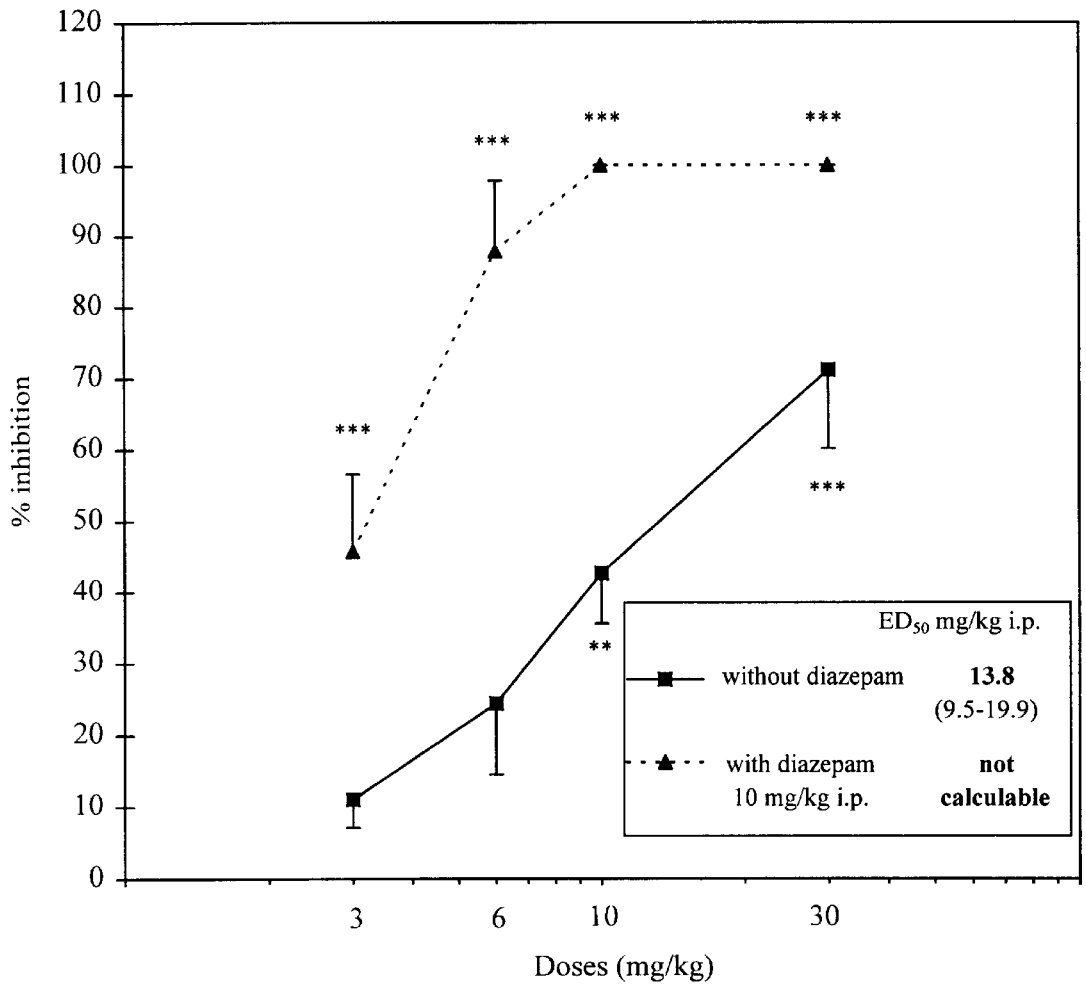
FIG. 4 graphically illustrates the effect of diazepam (10 mg/kg i.p.) on UP 202-56-induced antinociception in the hot plate test (56° C.) in mice.
Figure 5:
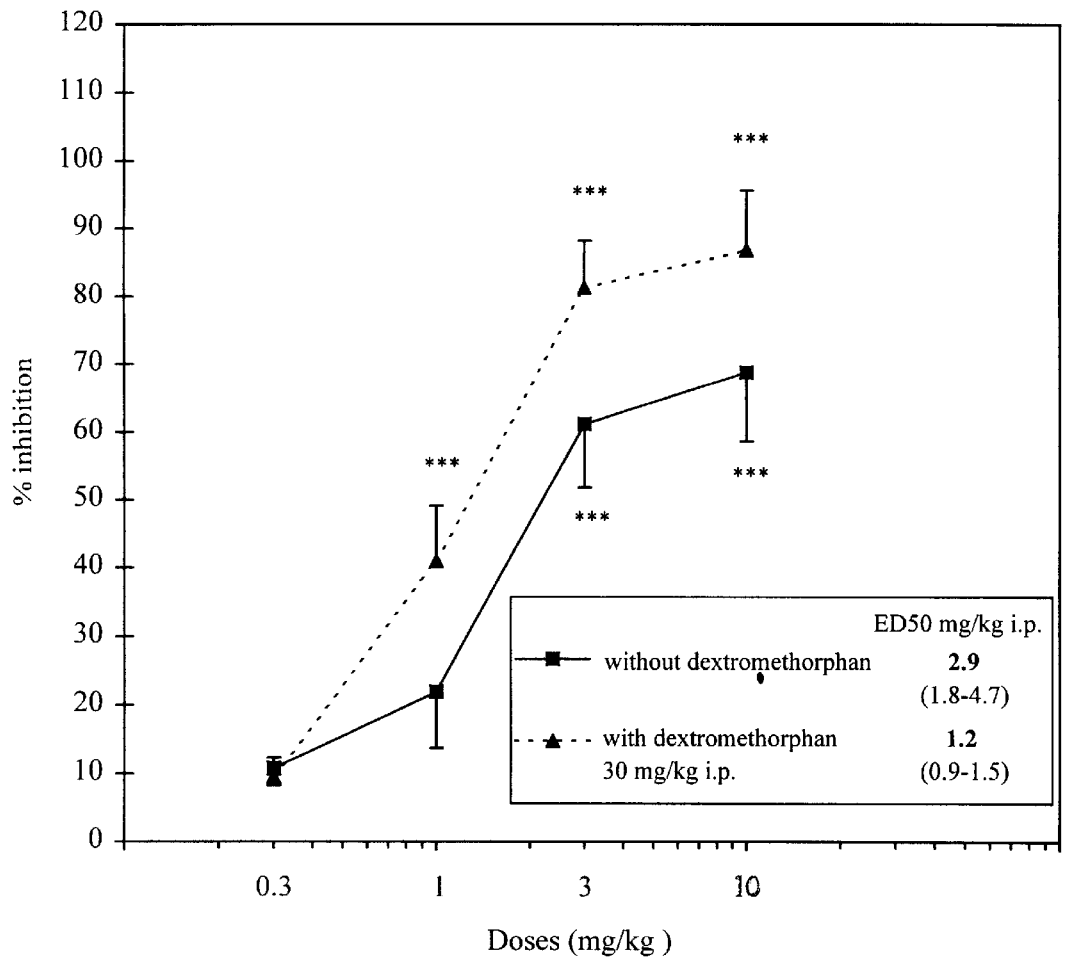
FIG. 5 graphically illustrates the effect of dextromethorphan (30 mg/kg i.p.) on UP 202-39-induced antinociception in the hot plate test (56° C.) in mice.

The results obtained are represented in FIGS. 1 to 5 which clearly show the potentiation effect exerted by morphine (FIGS. 1 and 2), by diazepam (FIGS. 3 and 4) upon the adenosinergic agonist compounds UP 202-39 and UP 202-56, as well as by dextromethorphan upon the compound UP 202-39.

Several examples of pharmaceutical compositions according to the invention are now given:

EXAMPLE 1

UP 202-56/DEXTROMETHORPHAN COMBINATIONS

Example 1A: Capsule (size no. 1)

| | |
|---|---|
| UP 202-56 | 10 mg |
| Dextromethorphan | 20 mg |
| Microcrystalline cellulose | 100 mg |
| Hydroxypropyl methyl cellulose | 10 mg |
| Magnesium stearate | 5 mg for a capsule |

Example 1B: Tablet

| | |
|---|---|
| UP 202-56 | 10 mg |
| Dextromethorphan | 20 mg |
| Microcrystalline cellulose | 100 mg |
| Lactose | 100 mg |
| Hydroxypropyl methyl cellulose | 10 mg |
| Magnesium stearate | 5 mg |
| Hydroxypropyl cellulose | 50 mg for a tablet |

Example 1C: Suppository

| | |
|---|---|
| UP 202-56 | 20 mg |
| Dextromethorphan | 40 mg |
| Semi-synthetic glyceride (suppocire) | 1,920 mg for a suppository |

Example 1D: Ophthalmic solution

| | |
|---|---|
| UP 202-56 | 0.03% |
| Dextromethorphan | 0.06% |
| Castor oil (Cremophor EL) | 5.% |
| Polysorbate 80 | 1.% |
| Water preparation for injections q.s.p. | 100% |

Example 1E: Injectable preparation

| | |
|---|---|
| UP 202-56 | 0.03% |
| Dextromethorphan | 0.06% |
| PEG 400 | 40% |
| Ethyl alcohol | 10% |
| Water preparation for injection q.s.p. | 100% |

EXAMPLE 2

UP 202-56/DIAZEPAM COMBINATIONS

Example 2A: Capsule (size no. 1)

| | |
|---|---|
| UP 202-56 | 10 mg |
| Diazepam | 10 mg |
| Microcrystalline cellulose | 100 mg |
| Hydroxypropyl methyl cellulose | 10 mg |
| Magnesium stearate | 5 mg for a capsule |

Example 2B: Tablet

| | |
|---|---|
| UP 202-56 | 10 mg |
| Diazepam | 10 mg |
| Microcrystalline cellulose | 100 mg |
| Lactose | 100 mg |
| Hydroxypropyl methyl cellulose | 10 mg |
| Magnesium stearate | 5 mg |
| Hydroxypropyl cellulose | 50 mg for a tablet |

Example 2C: Suppository

| | |
|---|---|
| UP 202-56 | 20 mg |
| Diazepam | 20 mg |
| Semi-synthetic glyceride (suppocire) | 1,920 mg for a suppository |

Example 2D: Ophthalmic solution

| | |
|---|---|
| UP 202-56 | 0.03% |
| Diazepam | 0.03% |
| Castor oil (Cremophor EL) | 5% |
| Polysorbate 80 | 1% |
| Water preparation for injection q.s.p. | 100% |

Example 2E: Injectable preparation

| | |
|---|---|
| UP 202-56 | 0.03% |
| Diazcpam | 0.03% |
| PEG 400 | 40% |
| Water preparation for injections q.s.p. | 100% |

EXAMPLE 3

UP 202-56/MORPHINE SULPHATE COMBINATIONS

Example 3A: Capsule (size no. 1)

| | |
|---|---|
| UP 202-56 | 10 mg |
| Morphine sulphate | 10 mg |
| Microcrystalline cellulose | 100 mg |
| Hydroxypropyl methyl cellulose | 10 mg |
| Magnesium stearate | 5 mg for a capsule |

Example 3B: Tablet

| | |
|---|---|
| UP 202-56 | 10 mg |
| Morphine sulphate | 10 mg |
| Microcrystalline cellulose | 100 mg |
| Lactose | 100 mg |
| Hydroxypropyl methyl cellulose | 10 mg |
| Magnesium stearate | 5 mg |
| Hydroxypropyl cellulose | 50 mg for a tablet |

Example 3C: Suppository

| | |
|---|---|
| UP 202-56 | 20 mg |
| Morphine sulphate | 20 mg |
| Semi-synthetic glyceride (suppocire) | 1.920 mg for a suppository |

Example 3D: Ophthalmic solution

| | |
|---|---|
| UP 202-56 | 0.03% |
| Morphine sulphate | 0.03% |
| Castor oil (Cremophor EL) | 5% |
| Polysorbate 80 | 1% |
| Water preparation for injections q.s.p. | 100% |

Example 3E: Injectable preparation

| | |
|---|---|
| UP 202-56 | 0.03% |
| Morphine sulphate | 0.03% |
| PEG 400 | 40% |
| Ethyl alcohol 10% | |
| Water preparation for injections q.s.p. | 100% |

We claim:

1. A pharmaceutical composition comprising, as active principle, a combination of an adenosinergic agonist and a compound selected from the group consisting of, a benzodiazepine and an N-Methyl-D-aspartic acid (NMDA) antagonist and a pharmaceutically acceptable carrier or excipient wherein the adenosinergic agonist compound is selected from the group consisting of N-cyclopropyl-1-deoxy-1-[6-[[2-[1-[2-(1-piperidinyl) ethyl] ethyl]-1H-indol-3-yl] ethyl] amino]-9H-purin-9-yl]β-D-ribofuranuronamide and N-cyclopropyl-1-deoxy-1-[6-[[2-[1-[(2,5-dimethylphenyl) methyl]-5-methyl-1H-indol-3-yl] ethyl] amino]-9H-purin-9-yl] β-D-ribofuranuronamide.

2. The pharmaceutical composition according to claim 1, wherein said benzodiazepine is diazepam.

3. The pharmaceutical composition according to claim 1, wherein said NMDA antagonist compound is dextromethorphan.

4. The pharmaceutical composition according to claim 1, wherein said composition is in a form suitable for administration via the oral route, via the parenteral route, via the rectal route, via the ocular route, via the transdermal route, via the nasal route, or via the auricular route.

5. The pharmaceutical composition according to claim 6, wherein the weight ratio of the adenosinergic agonist compound to the compound selected from the group consisting of the benzodiazepines and NMDA antagonists, is between 0.1 and 1.

6. The pharmaceutical composition according to claim 1, wherein said composition is in the form of a unit dose containing from 5 mg to 200 mg of adenosinergic agonist compound.

* * * * *